United States Patent [19]
Falk

[11] Patent Number: 5,850,255
[45] Date of Patent: Dec. 15, 1998

[54] METHOD AND APPARATUS FOR IMAGING ELECTRIC FIELDS

[75] Inventor: R. Aaron Falk, Renton, Wash.

[73] Assignee: Optometrix, Inc., Renton, Wash.

[21] Appl. No.: 733,257

[22] Filed: Oct. 18, 1996

[51] Int. Cl.$^6$ ............................................. H04N 5/30
[52] U.S. Cl. ................................. 348/162; 348/329
[58] Field of Search .................... 348/162, 329; 372/102; 359/7; 385/8; 346/160; 350/354

[56] References Cited

U.S. PATENT DOCUMENTS

| | | | |
|---|---|---|---|
| 4,635,082 | 1/1987 | Domoto et al. | 346/160 |
| 4,715,689 | 12/1987 | O'Meara et al. | 350/354 |
| 5,150,228 | 9/1992 | Liu et al. | 359/7 |
| 5,239,598 | 8/1993 | Wright et al. | 385/8 |
| 5,325,129 | 6/1994 | Henry et al. | 348/162 |
| 5,729,285 | 3/1998 | Peterson et al. | 348/162 |

OTHER PUBLICATIONS

2449–58, Dec. 1990, L. E. Kingsley et al.

R.A. Falk, et al., "Optical Probe Techniques for Avalanching Photoconductors,", Proc. 8th IEEE Pilsed Power Conference: 29–32, 1991.

K. H. schoenbach, et al., "Electric Field Measurements in Photoconductive GaAs Switches," Proc 8th IEEE Pulsed Power Conference: 105–8, 1991.

K. H. Schoenbach, et al., "Optical Measurements of the Electirc Field and Temperature Distribution in Photoconductive GaAs Switches," SPIE 1632: 54–64, 1992.

R. A. Falk, et al., "Dynamic Optical Probing of High–Power Photoconductors," 9th IEEE Pulsed Power Conference: 88–91, 1994.

J. C. Adams et al., "Below Band–Gap Electro–absorption in Bulk Semi–Insulating GaAs," Appl. Phys. Lett. 63: 633–5, 1993.

W. R. Donaldson, et al., "Electro–Optic Imaging of the Internal Fields in Hig–Power Photoconductive Switches," J. Appl. Phys. 68: 6453–7, 1990.

L. E. Kingsley, et al., "Electrooptic Imaging of Surface Electric Fields in High–Power Photoconductive Switches," IEEE Trans. on Electron Devices 37: 2449–58, 1990.

W. R. Donaldson, "Optical Probing of Field Dependent Effects in GaAs Photoconductive Switches," Proc 8th IEEE Pulsed Power Conference: 45–9, 1991.

W. R. Donaldson, et al., "The Effects of Doping on Photoconductive Switches as Determined by Electro–Optic Imaging," SPIE 1632: 88–97, 1992.

B. H. Kolner, et al., "Electro–Optic Sampling In GaAs Integrated Circuits," IEEE J. Quantum Electronics 22: 79–93, 1986.

K. J. Weingarten, et al., "Picosecond Optical Sampling of GaAs Integrated Circuits," IEEE J. Quantum Electronics 24: 198–220, 1988.

R. A. Falk, et al., "Direct Electo–Optic Measurement of the Internal Electric Fields of GaAs Photoconductive Switches," SPIE 2343: 2–13, 1994.

R. A. Falk, et al., "Electro–Optic Imagery of High–Voltage GaAs Photoconductive Switches," IEEE Trans. Electron Devices 42:43–9, 1995.

J. C. Adams, et al., "Electro–Optic Imagery of Internal Fields in (111) GaAs Photoconductors," IEEE Trans. Electron Devices 42: 1081–5, 1995.

*Primary Examiner*—Tommy P. Chin
*Assistant Examiner*—Gims Philippe

[57] ABSTRACT

An optical beam (2) passes through a polarizer (10), a target (24), an analyzer (20) and onto a camera (22) where a plurality of images are formed. The images are digitized by a frame grabber (30) and processed by a general purpose computer (32) to form electric field images of the target.

13 Claims, 6 Drawing Sheets

METHOD AND APPARATUS FOR IMAGING ELECTRIC FIELDS

FIELD OF THE INVENTION

This invention relates to methods and apparatus for imaging the electric field in an electro- optically active target, more specifically, methods and apparatus for obtaining quantitative, self-calibrating image of the internal electric field of an electrical device fabricated from an electro-optic substrate are described.

BACKGROUND OF THE INVENTION

Images showing the distribution of the electric field within gallium arsenide (GaAs) devices have been made in the past using the electro-absorption or Franz-Keldysh effect as described in, "Optical Probe Techniques for Avalanching Photoconductors", R. A. Falk, J. C. Adams, and G. Bohnhoff-Hlavacek, Proc. 8th IEEE Pulsed Power Conference, 29–32 (1991), "Electric Field Measurements in Photoconductive GaAs Switches", K. H. Schoenbach, J. S. Kenney, A. Koenig, B. J. Ocampo, R. F. K. Germer, and H. J. Schultz, Proc. 8 th IEEE Pulsed Power Conference, 105-8(1991), "Optical Measurements of the Electric Field and Temperature Distribution in Photoconductive GaAs Switches", K. H. Schoenbach, J. S. Kenney, and R. J. Allen, SPIE 1632, 54-64(1992), and "Dynamic Optical Probing of High-Power Photoconductors", R. A. Falk, J. C. Adams, and S. G. Ferrier, 9 th IEEE Pulsed Power Conference, 88-91 (1994). In this technique, the device is optically probed with a probe wavelength lying along the GaAs absorption edge, typically between 880 and 920 nanometers. After passing through the device, the optical probe is directed toward a camera and an image is recorded. As described in "Below Band-Gap Electro-absorption in Bulk Semi-Insulating GaAs", J. C. Adams, C. D. Capps, R. A. Falk, and S. G. Ferrier, Appl. Phys. Lett. 63, 633-5(1993), changes in the electric field inside the GaAs device change the amount of probe light which is absorbed by the device. These changes in absorption result in a recorded image intensity variation which is related to the electric field inside the GaAs device.

Although this electro-absorption imaging technique produces extremely revealing qualitative information, the method proves difficult to calibrate due to the rapid changes in electro-absorption with electric field. In addition, these rapid changes severely limit the range of electric field data available in a single image. A further complicating feature of electro-absorption imagery is the changes which occur in absorption in GaAs due to changes in temperature. In an active electronic GaAs device, both thermal and electric field changes will occur. Separation of these two absorption effects is often intractable. Finally, electro-absorption imagery is only an option in limited, electro-optically active materials such as GaAs. Other electro-optic materials such as lithium tantalate or lithium niobate cannot be probed in this manner.

A more general technique for imaging the electric fields of electronic devices utilizing external electro-optic crystals has been described, "Electro-Optic Imaging of the Internal Fields in High-Power Photoconductive Switches", W. R. Donaldson, L. Kingsley, M. Weiner, A. Kim, and R. Zeto, J. Appl. Phys. 68, 6453–7(1990), "Electrooptic Imaging of Surface Electric Fields in High-Power Photoconductive Switches", L. E. Kingsley, and W. R. Donaldson, IEEE Trans. on Electron Devices 37, 2449–58(1990), "Optical Probing of Field Dependent Effects in GaAs Photoconductive Switches", W. R. Donaldson, Proc. 8 th IEEE Pulsed Power Conference, 45–9(1991), and "Effects of Doping on Photoconductive Switches as Determined by Electro-Optic Imaging", W. R. Donaldson, and L. Mu, SPIE 1632, 88–97 (1992). In this technique, an external electro-optic crystal, such as lithium tantalate is placed in close proximity to the electronic device being tested. Fringing fields form the test device enter the external crystal which change the crystal birefringent properties. A polarized optical probe passes through the crystal, reflects from a dielectric mirror on the back side and returns to a polarization sensitive camera. The optical system is arranged such that the image intensity at the camera is related to the changes in polarization of the optical probe caused by the electric field in the crystal. This image is typically digitized and processed to produce and image whose intensity is directly proportional to the fringing electric fields in the external crystal.

Several difficulties occur in utilizing the external crystal approach. First, the fringing electric fields in the external crystal may not truly represent the fields internal to the test device. In particular, surface charges on the test device will mask its internal field structure. In addition, use of an external crystal will perturb the electric field lines in the device due to the high dielectric constant of the crystal. More importantly, use of an external crystal limits the possible interaction geometries and can often require undue modifications of the test device, e.g. the test device may need to be sliced in half in order to place the crystal transverse to the contacts. Finally, the external crystal methodology requires a calibration process which assumes initial field uniformity; an assumption which is not valid in all applications.

Electro-optic sampling at a single point within an electro-optically active device has been also been performed and described in "Electro-Optic Sampling In GaAs Integrated Circuits", B. H. Kolner, and D. M. Bloom, IEEE J. Quantum Electronics 22, 79–93 (1986) and "Picosecond Optical Sampling of GaAs Integrated Circuits", K. J. Weingarten, M. J. W. Rodwell, and D. M. Bloom, IEEE J. Quantum Electronics 24, 198–220(1988). The apparatus described therein was directed towards high-speed pulse-probe sampling of the time dependent behavior of electronic circuits. The additional features required to produce electric field images are not present in this apparatus, leaving the apparatus incapable of producing images. Specifically, the need for 1) an imaging detector, 2) methodology for image capture, digitization, storage and display, and 3) calibration and extraction of an electric field image from the initial raw image data, especially as concerns areas of the image which contain voids, were not described.

The present invention is directed towards overcoming the foregoing and other disadvantages. More specifically, the presented invention is directed to providing a self-calibrating, automated method for producing images whose intensity is directly proportional to the internal electric field of the test device.

SUMMARY OF THE INVENTION

The present invention provides a self-calibrating arrangement for quantitatively imaging the internal electric field of electrical devices fabricated from electro-optically active material. The electric field imaging system according to the present invention comprises an optical beam whose state and orientation of polarization are set by a polarizer. The polarized optical beam then interacts with the electrical device in a fashion which allows the internal electric field of the device to produce changes in. After passing through the device, the optical beam then passes through an analyzer. The analyzer causes the changes in the polarization state and orientation of the optical beam to become amplitude variations in the optical beam. These amplitude variations are then detected by an electronic camera. The electronic image produced by the camera is digitized and pixelated using a frame grabber, processed in a general purpose computer and then displayed.

In operation, electric field imaging system obtains three images, one with the electrical device in an inactive condition and two with the electrical device in an active condition. The latter two images are obtained utilizing two different states of the polarizer and analyzer. The combination of these three image is then analyzed digitally to produce the calibrated electric field image. The analysis comprises the steps of subtracting the first image from both of the second two images followed by dividing the latter two images. A step-wise process is then utilized to extract the electric field for each pixel in the image. The step-wise process includes means to handle exceptions where the optical beam did not pass through the device.

DETAILED DESCRIPTION OF THE INVENTION

Figure 1:
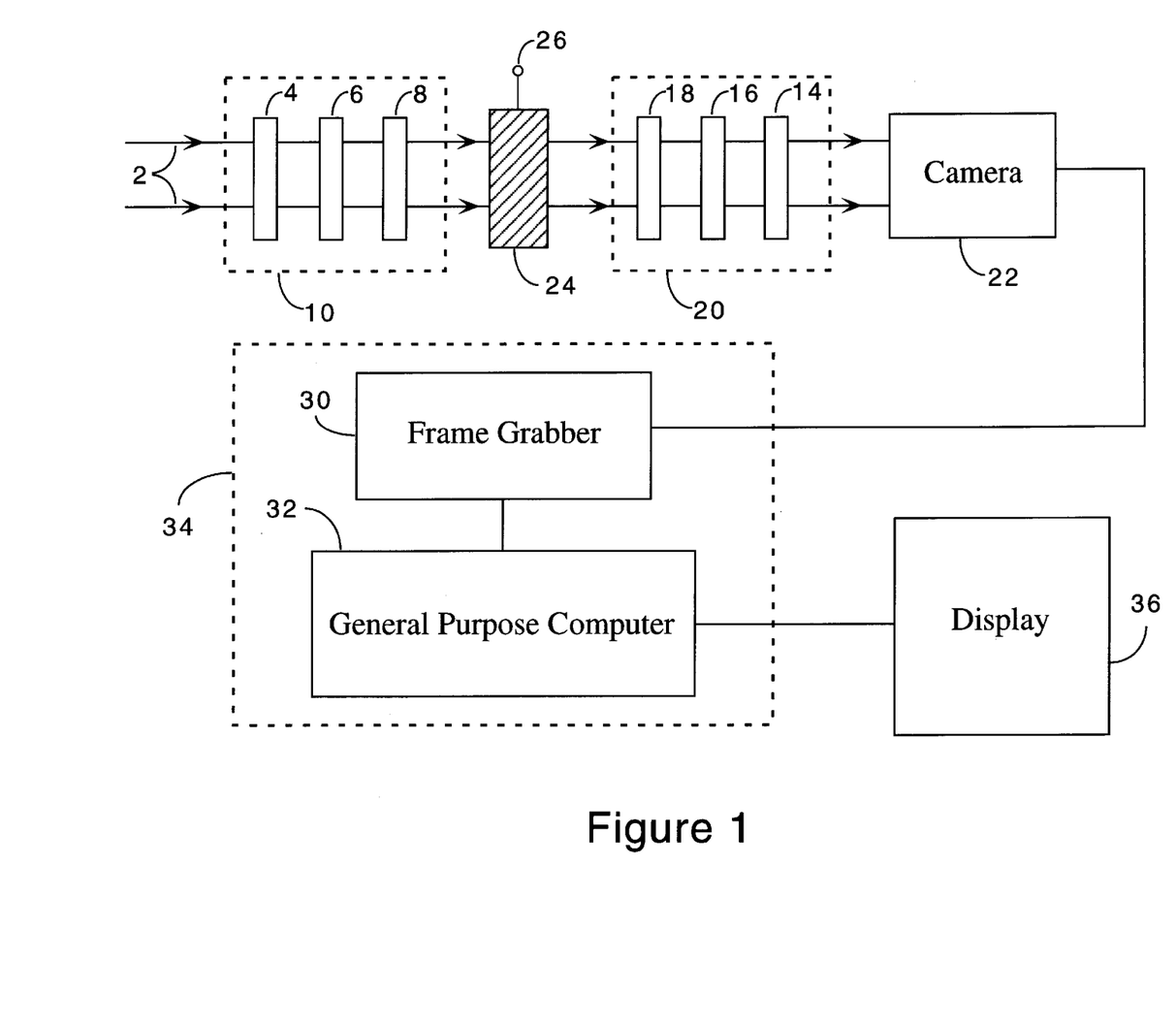
FIG. 1 is a schematic view of a transmission arrangement of the electric field imaging system.

FIG. 1 sets forth a preferred embodiment for a system for imaging the internal electric field of electrical devices fabricated in electro-optically active materials. Electro-optically active materials include most Ill-V compound semiconductors such as gallium arsenide (GaAs) and gallium phosphide (GaP), many II-IV compounds such as zinc selinide (ZnS) and several other compound crystals such as lithium tantalate ($LiTaO_3$) and barium titinate ($BaTiO_3$).

The imaging system includes an optical beam 2, which provides a source of optical radiation for the imaging system. The optical beam is indicated by lines and arrows with the lines representative of the optical rays of the optical beam and the arrows indicating the direction of propagation of the optical beam. The optical beam passes sequentially through a polarizer 10, a target 24, an analyzer 20, and is finally detected by an electronic camera 22. The target is an electrical device fabricated from an electro-optically active material and which is electrically activated through a set of electrical connections 24. The wavelength of the source of optical radiation is selected to be in a region for which the target material is transparent and will pass the optical beam without undue absorption. For example, if the target material is GaAs, a wavelength longer than about 1000 nanometers would be chosen in order to avoid the large absorption which occurs in GaAs at shorter wavelengths.

The purpose of the polarizer 10 is to set the initial state and orientation of polarization of the optical beam prior to passing through the target. As will be described in more detail below, the desired initial polarization state depends on the specific electro-optic material in the target, along with the orientation of the material crystal axis. The polarizer consists of a first linear polarizer 4, a first half waveplate 6, and a first quarter waveplate 8. The first linear polarizer sets the optical beam polarization state to be linear along a specific direction or orientation perpendicular to the propagation direction of the optical beam. Rotation of the first half waveplate about its optical axis, which is aligned with the propagation direction of the optical beam, allows the orientation of the linear polarization to be rotated around the propagation direction. Rotation of the first quarter waveplate about its optical axis, which is aligned with the propagation direction of the optical beam, allows the state of polarization to be transformed from linear to elliptical. It is known in the field of optics that the combination of theses three items, the first linear polarizer, first half waveplate, and first quarter waveplate, contained in the polarizer 10 allows any arbitrary initial state of polarization to be obtained in an optical beam.

The purpose of the analyzer 20 is to vary the intensity of optical beam in relation to its state and orientation of polarization after passing through the target. The analyzer consists of a second linear polarizer 14, a second half waveplate 16, and a second quarter waveplate 18. The analyzer operates in a reverse fashion to the polarizer and it is well known in the field of optics that the combination of these three elements, the second linear second, second half waveplate, and second quarter waveplate, allows any arbitrary polarization to be analyzed.

The spatial variation in intensity of the analyzed optical beam is captured by the electronic camera 22. In the preferred embodiment an electronic camera such as a charge coupled device (CCD) camera is used. The electronic image from the electronic camera is feed into a frame grabber 30 where it is digitized and stored in binary format. The frame grabber is connected to a general purpose computer 32 which allows processing and visual display of images on a display 36. The frame grabber and general purpose computer constitute an image storage and processing unit 34, which can be implemented electronically in a variety of forms.

Figure 2:
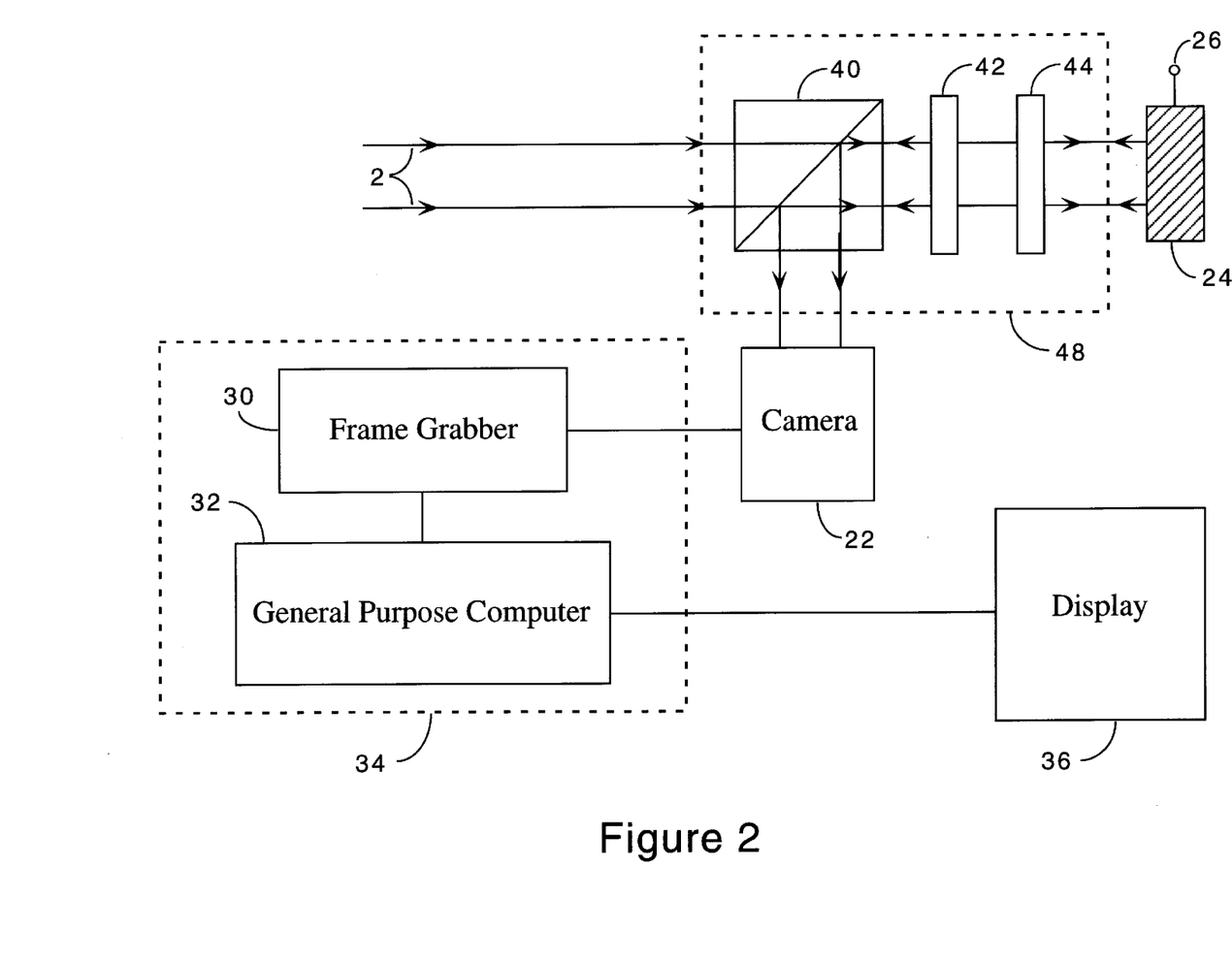
FIG. 2 is a schematic view of a reflection arrangement of the electric field imaging system.

The embodiment shown in FIG. 1 is appropriate when the optical beam can readily pass completely, through the target. This embodiment is referred to as transmission imaging. Many potential targets will contain elements which block the path of the optical beam and are not suitable for transmission imaging. In particular, semiconductor devices often contain metal contact layers which will block the optical beam. For these devices, a second, reflection imaging, embodiment is shown in FIG. 2. In this embodiment, the optical beam 2 passes through the a polarizer/analyzer 48 which first sets the polarization state of the optical beam and directs it towards the target 24, i.e. the polarizer/analyzer 48 behaves analogously to the polarizer 10 in FIG. 1. The optical beam in FIG. 2 first passes through the top surface of the target, through the body of the target and strikes the bottom surface of the target. In the case of a semiconductor or similar device, the target is oriented so that the blocking metalization is on the bottom surface and acts as a mirror to reflect the optical beam back through the body of the target and towards the polarizer/analyzer. The reflected optical beam then passes back through the polarizer/analyzer, but in an opposite direction from the first transit. On this second pass the polarizer/analyzer 48 behaves analogously to the analyzer 20 in FIG. 1, except that the analyzed optical beam is deflected at right angles towards the electronic camera 22. The remainder of the reflection imaging system in FIG. 2 is identical to the transmission mode system in FIG. 1.

The polarizer/analyzer 48 in FIG. 2 consists of a polarizing beam splitter 40, a half waveplate 42 and a quarter waveplate 44. The polarizing beam splitter (PBS) is a particular type of linear polarizer in which an optical beam with one orientation of linear polarization passes directly through the PBS while the orthogonal orientation of linear polarization is deviated at right angles. Thus, when the optical beam passes through the polarizer/analyzer 48 from the PBS to the quarter waveplate, it behaves analogously to the polarizer 10 in FIG. 10. When the optical beam passes through the polarizer/analyzer 48 in the opposite direction it behaves analogously to the analyzer 20 in FIG. 1, except that the optical beam is directed at right angles towards the electronic camera 22. The only difference in functionality of the separate the polarizer 10 and analyzer 20 and the polarizer/analyzer 48 is that the former combination allows more flexibility in the settings of the waveplates contained in each unit. This reduction is not significantly detrimental to obtaining the desired electric field imaging functionality, however. Thus, for the current invention, the two embodiments in FIGS. 1 and 2 are functionally identical and only seek to optimize the optical interface with the target.

Figure 3:
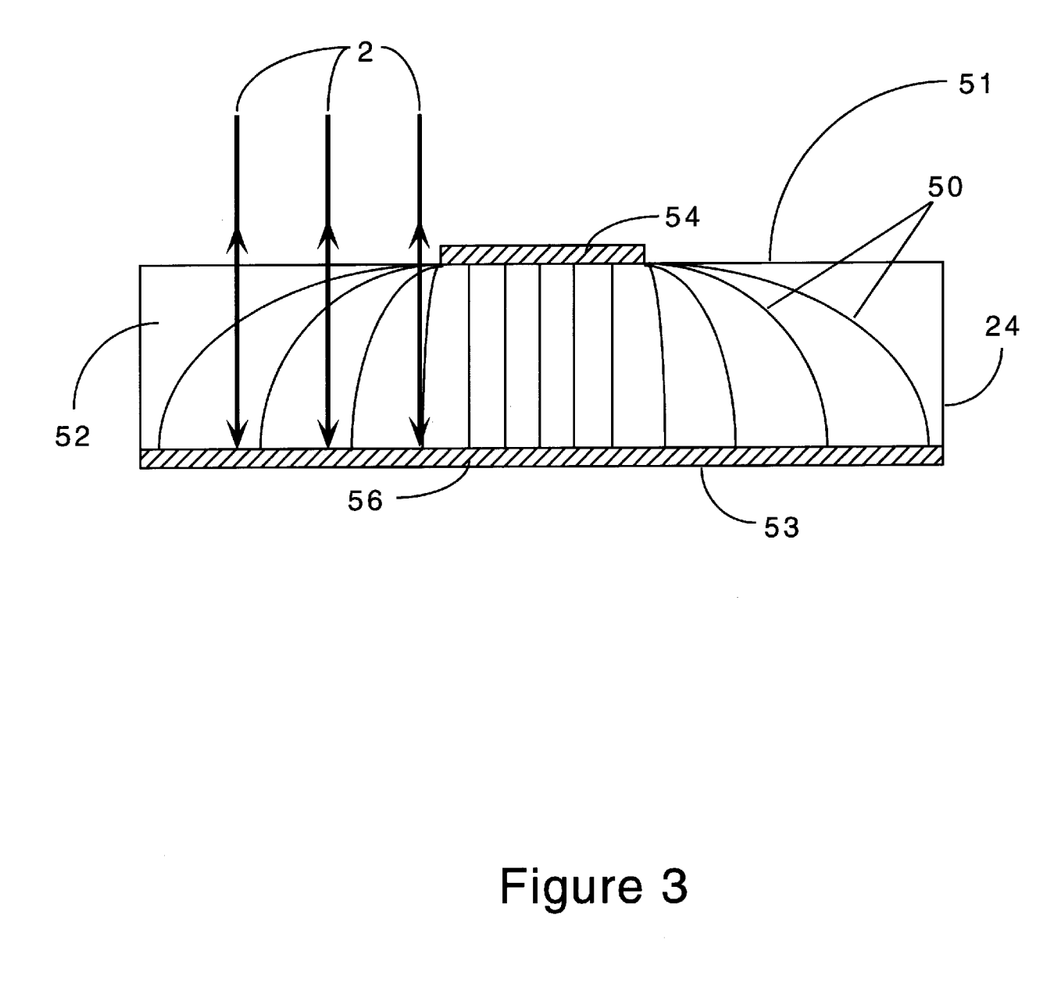
FIG. 3 is a detail schematic of the interaction of the optical beam with the target.

The interaction of the optical beam with the target for the reflection imaging embodiment in FIG. 2 is shown in more detail in FIG. 3. The target 24 is presumed to be fabricated from an electro-optically active substrate 52 such as GaAs and having a top surface 51 and a bottom surface 53. As shown in FIG. 3 a top electrical contact 54 covers a part of the upper surface of the target and a bottom electrical contact 56 covers the entire bottom surface of the target. This type of bottom electric contact is typical for many electronic devices. For a GaAs electronic device, the electrical contacts will typically be metallic and thereby behave as a mirror. However, even if the bottom contact is not present, the refractive index changes at the bottom surface will cause a mirror like reflection to occur. As shown in FIG. 3, the optical beam passes through the top surface of the target, reflects off the bottom surface and returns along the beam path. Reflections will also occur at the top surface of the target and the top electrical contact. These latter two reflections contribute to a background in the optical beam. When a voltage is applied between the top electrical contact 54 and the bottom electrical contact 56, an electric field will be present in the target 24 causing electric field lines 50 to be present. The electric field lines cause changes in the birefringence of the electro-optically active substrate 52 which in turn affect the polarization state of the optical beam 2 upon passing through the target.

Returning to FIG. 2, the electronic camera 22 records an image of the target with the image intensity related to the electric field within the target. Ignoring for the moment any background contributions to the optical beam entering the electronic camera, the relationship between the intensity at a particular pixel can be understood by use of Jones vector notation. The basic analysis for this optical configuration has been previously performed for a GaAs target in "Gallium Arsenide Integrated Circuit Testing Using Electrooptic Sampling", K. J. Weingarten Dissertation, Stanford University (1987) for a non-imaging system. Other substrates will behave similarly. The result for an imaging system is given by $$A(x,y) = A_0(x,y)\{\sin(2\theta)\cos(\delta(x,y)) + \sin(\delta x,y))\cos(2\theta)\sin(2\theta + 2\gamma - 4\phi)\} \quad (1)$$

where (x) and (y) are spactial coordinates in the camera image plane, (A) is the amplitude as a function of image position, and ($A_O$) is the polarization independent amplitude at the imaging plane, i.e. it is the initial optical beam amplitude times factors accounting for the transmission losses through the optical system. ($\theta$), ($\phi$), and ($\gamma$) are the rotation angles about the optical beam axis of the quarter wave plate, the half wave plate, and the target respectively. The zero reference for these three angles is the direction of linear polarization resulting from the PBS after the first transit of the optical beam. ($\delta$) is the electro-optic phase shift due to the presence of the electric field lines in the target. The amplitude is seen to be an oscillatory function of ($\delta$) with ($\theta$), ($\phi$) and ($\gamma$) affecting the phase and amplitude of the oscillations. The intensity recorded by the imaging system is the square of Equation (1). In general the intensity will have an additional offset term due to scattering from the optical components and reflection from the front surface of the target.

Equation (1) is appropriate for the reflection imaging system in FIG. 2. A similar equation describes the image intensity for the transmission system in FIG. 1. More generally, the recorded intensity variation due at a specific camera spatial position is given by the form $$I = I_0\{\sin(2kV_p + \epsilon) + C\} \quad C \geq 1 \quad (2)$$

with where ($I_o$) and (C) are constants dependent on the optical arrangement. ($I_o$) accounts for the polarization independent transmission losses and (C) accounts for background scattering and reflections from optical elements and the target, ($\epsilon$) is a phase constant dependent on the waveplate orientations, (k) is the electro-optic coefficient of the electro-optically active substrate, which depends on the optical propagation direction, the target crystal axis and electric field direction. Finally, ($V_p$) is defined as the path voltage.

As a specific example, we will analyze the electro-optic effect in GaAs for the reflection imaging technique shown in FIG. 2. Note however, that the analysis applies more generally to all optically active media as well as the transmission imaging technique shown in FIG. 1. For typical GaAs devices, the [100] crystal axis is perpendicular to the top surface and therefore parallel to the optical path as shown in FIG. 3. The electro-optic tensor of GaAs is such that for these propagation conditions, only the component of the electric field along the [100] axis contributes to the electro-optic effect. In this case, $$k = \frac{2\pi n_0^3 r_{41}}{\lambda_0} \text{ and } V_p = \frac{1}{2} \oint E \cdot dz \quad (3)$$

where ($n_o$) is the index of refraction of GaAs with value of 3.6, ($r_{14}$) is an electro-optic coefficient with a value of 1.4 * $10^{-12}$ (m/V) ($\lambda_o$), is the operational wavelength (nominal 1000 nanometers) and (z) is the axis of propagation of the optical beam. Using these parameters, (k) has a value of 4.1 * $10^{-4}$ (rad/V).

It is noted that ($V_p$) is the total voltage drop along the optical beam path and only the z component of the electric field contributes. Therefore the measured quantity, ($V_p$), is a path voltage and not the actual electric field. Thus, the resultant image at the electronic camera is not a direct image of electric field lines, but a related image of the potential drop along the optical path. For the present invention, the terms electric field image and path voltage image will be considered interchangeable, with the connection between electric field and path voltage defined in Equation (3).

Analysis of the images as represented by Equation (3) involves inverting the equation to extract the path voltage as a function of position. This inversion presents some special difficulties. The most important problem is that for an image containing a large range of path voltages, the intensity becomes a multi-valued function of $V_p$. Additionally, the constants ($I_o$) and (C) in Equation (2) are typically functions of image position and may not be easily obtained through calibration means.

The method of analysis used here starts with the following assumptions:
1) the phase, ($\epsilon$), can be set to zero and 90 degrees through rotation of the waveplates,
2) $I_o$ and C are independent of the waveplate orientation and any voltage applied to the target electrical contacts.

Figure 4:
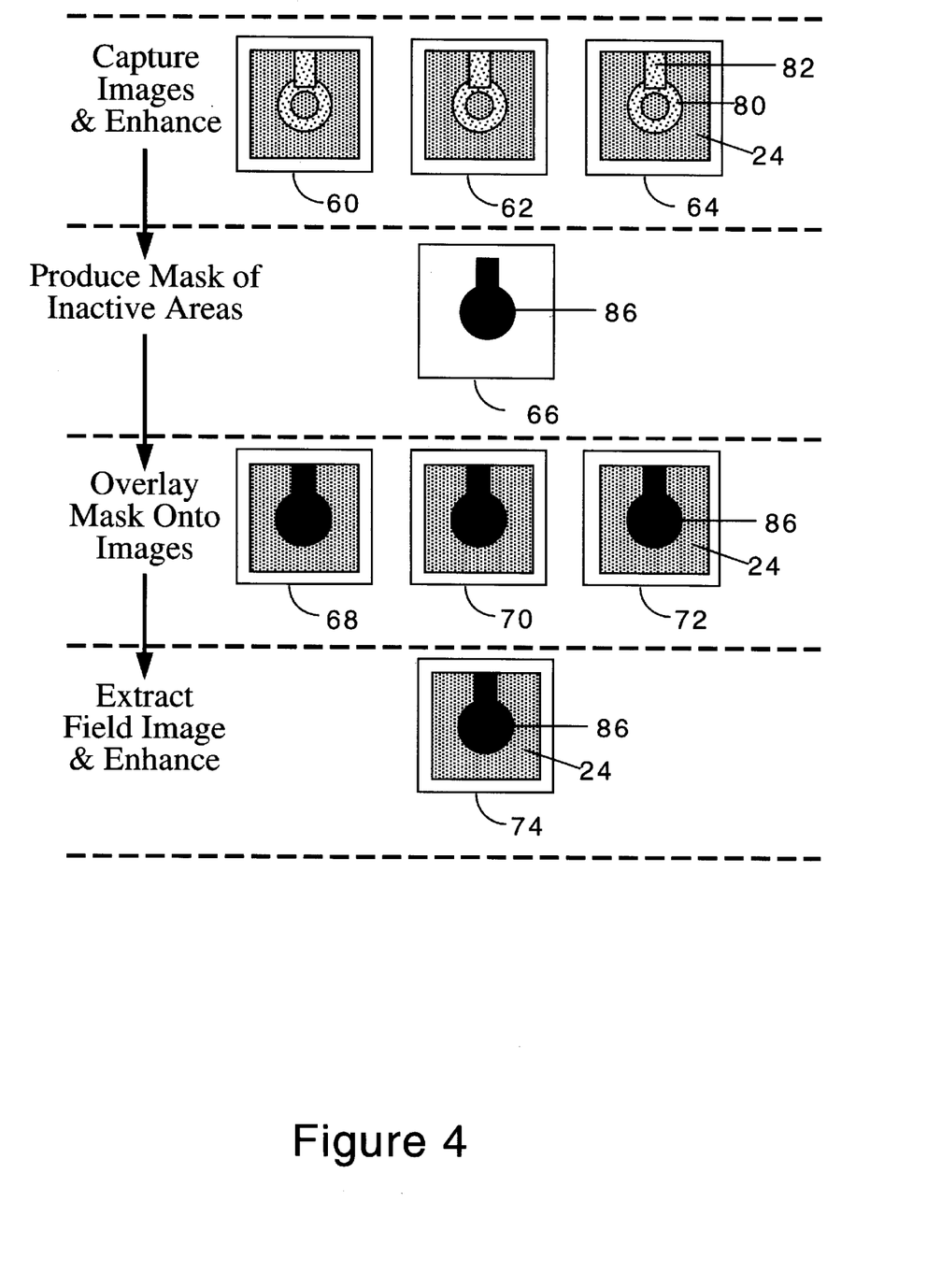
FIG. 4 is a functional diagram of the image processing steps required to extract an electric field image from the raw starting images.

The method for extracting the phase (2 $kV_p$) for each image position under these assumptions is indicated schematically in FIG. 4. Four process steps are indicated by four labels on the left side of FIG. 4 with arrows indicating the process flow between the steps. To the right of each label are schematics of images related to each step which are separated by dashed lines.

In the first process step "Capture Images & Enhance", three electronic images are obtained, a background image 60 for which the applied voltage and $\epsilon$ are set to zero, an X image 62 with voltage present and with $\epsilon$ at zero, and a Y image 64 at the same applied voltage, but with set to 90 degrees. These images are captured by the frame grabber 30 which both pixelates the images and produces a digital word for each pixel whose value is proportional to the intensity, I, at the related image position. Each of these three images is spatially registered with each other, i.e. the position and scale of the target image is not changed. If the images are not registered during capture, computer image processing techniques can be used to spatially shift and scale the images in order to obtain registration. Equations describing the image intensity at each pixel for the three images are given by Background image–$I_B{}^{ij}=I_0{}^{ij}C^{ij}$ (4)

X image–$I_x{}^{ij}=I_0{}^{ij}\{\sin(2kV_p{}^{ij})+C^{ij}\}$ (5)

and

Y image–$I_y{}^{ij}=I_0{}^{ij}\{\cos(2kV_p{}^{ij})+C^{ij}\}$ (6)

where (i) and (j) are the pixel row and column numbers respectively. After the three images are captured they may be digitally enhanced by the general purpose computer. For example, speckle resulting from use of a laser as the optical source may by reduced by smoothing the image. However, any enhancement algorithms must not change the basic relationship between the images indicated in Equations (1–3). At this point areas of the image which do not include the target may be clipped.

Some areas of the captured images will contain components which will block the passage of the optical beam through the target such as contact metalization 80 and metallic attachment tabs 82 or simply do not contain the target. In these areas Equations (1–3) do not apply and later processing steps will not be valid. In order to correctly process these invalid areas in the image, a second process step "Produce Mask of Inactive Areas" is performed. For this second process step, an mask image 66 is produced which contains a digital mask 86. The mask covers all blocking areas such as the contact metalization and the metallic attachment tabs and any other areas of the three images for which later processing is invalid. The purpose of the mask is to indicate to the later processing steps those areas which are not to be processed. The mask can be produced either by an operator drawing the mask or by automated processes such as utilization of CAD drawings of the target. For tutorial discussions, the digital mask areas of the mask image are assumed to be black, i.e. a digital intensity value of zero, and all other areas of the mask image are assumed to be white, i.e. all bits in the digital word representing a pixel are set to one.

In the third process step "Overlay Mask Onto Images", the mask image is combined with the background, X and Y images to produce masked background image 68, masked X image 70 and masked Y image 72. In this tutorial example, the images are combined through use of a digital AND on a pixel-by-pixel basis. The digital AND will cause zeros to occur in every pixel where the digital mask is present and will not change the values of the pixels where the digital mask is not present. As a simultaneous zero in both the X and Y images is not physically possible for the electro-optic effect, the presence of simultaneous zeros can be used as marker by later processing steps to detect the mask areas and not process them. Simultaneous zeros in all three images can also be utilized as a marker with the added benefit of detecting pixels where the optical intensity is zero. Other marking means could also be used.

The forth processing step "Extract Field Image & Enhance" combines the three masked images to produce the final electric field image 74. This final process proceeds as follows for the non-masked areas. First the masked background image 68 is subtracted pixel-by-pixel from the masked X image 70 and the masked Y images. Dividing the two resultant images then produces an intermediate image array with pixel values given by $$\alpha^{ij} \equiv \frac{I_x^{ij} - I_B^{ij}}{I_y^{ij} - I_B^{ij}} = \tan(2kV_p^{ij}) \quad (7)$$

which now only depends on the path voltage and (k). The value of (k) is known from available sources of material properties of can be independently measured by known techniques.

Direct inversion of Equation (7) to extract the path voltage still has problems of phase redundancy. One method to circumvent this redundancy is to track the phase difference from pixel-to-pixel utilizing $$\Delta(2kV_p^{ij}) = 2k(V_p^{ij} - V_p^{nm}) - \arctan\left(\frac{\alpha^{ij} - \alpha^{nm}}{1 + \alpha^{ij}\alpha^{nm}}\right) \quad (8)$$

where ($^\theta$o) is an additive phase term relating to the initial choice of phase at the starting reference pixel, and (n), (m) identify the current reference pixel. For an image to be open to analysis, the value of Equation (8) must be less than 90 degrees. The additive phase term represents a dc bias level which can be separately calibrated or, noting that a path voltage is a relative measurement, may simply subtracted from the overall image. Dividing the result of Equation (9) by (2k) produces pixel values for the electric field image 74 in the non- masked areas. Pixel values in the marked areas are undefined and may be set to any convenient value, e.g. black.

The processing flow described in Equations (8) and (9) involves a sequence of calculations stepping from one pixel to another and using the previous pixel as a reference. One possible flow for this sequence of calculations is shown schematically in FIG. 5. In the figure, a pixel map 90 representing the rows and columns of the intermediate image array pixels with each pixel 92 represented by a white or black square. Black squares are part of the mask 86 and are not to be processed, while white squares are part of the intermediate image array. In this example, the upper left pixel is chosen as the initial reference pixel 96 for starting the calculations in Equations (8) and (9). The phase for the next pixel to the right is then calculated with respect to this reference using Equations (8) and (9). The process then proceeds down the first row using the previous pixel in the row as the phase reference. The phase of the first pixel in the next row is determine by using the first pixel in the row above as its reference. The row is filled in as described above and then the process repeats until the entire image is analyzed. This process flow is indicated by the process flow arrows 94.

Figure 5:
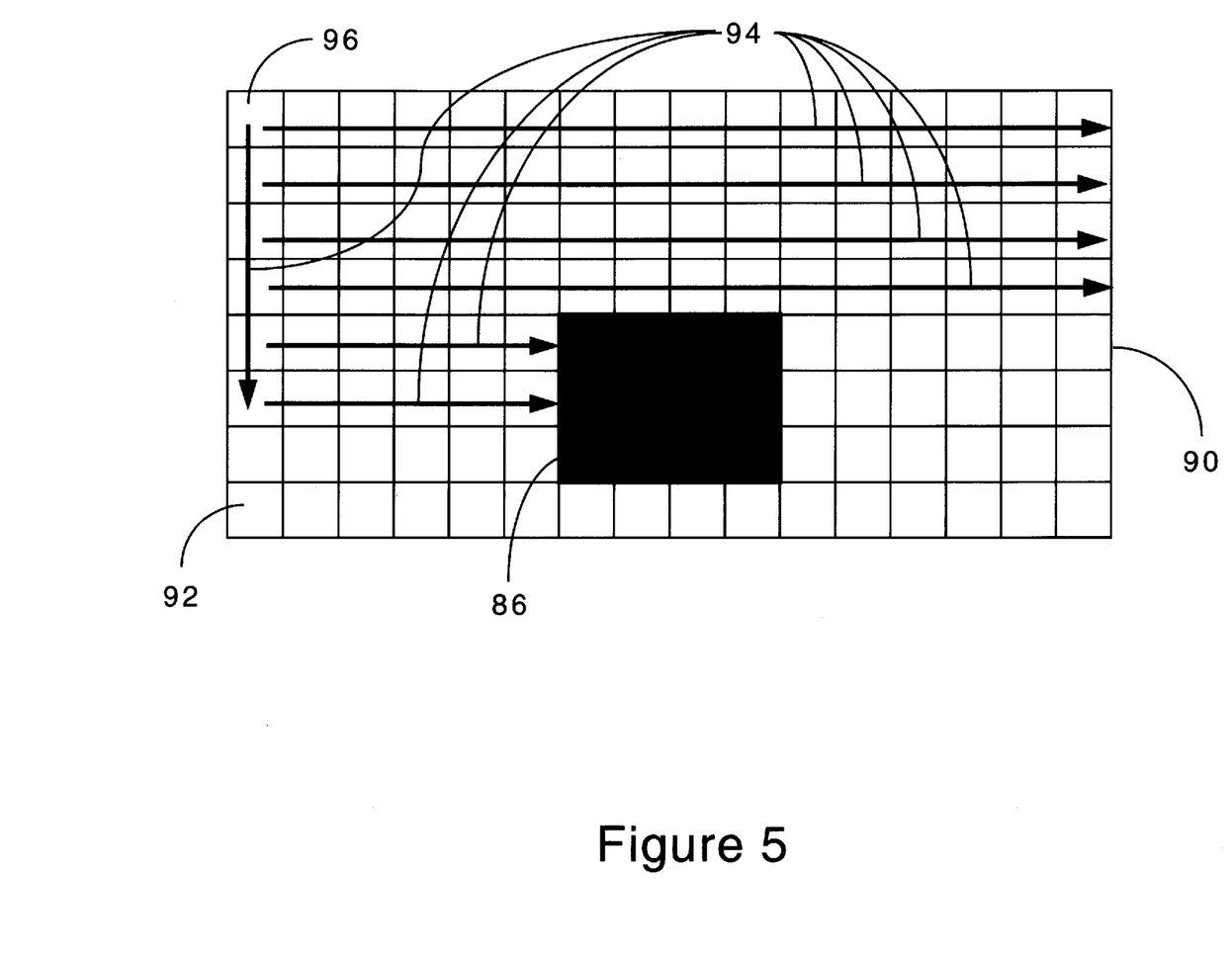
FIG. 5 is a schematic of the details of the phase extraction process for each pixel in the image which utilizes row-by-row processing techniques.

As seen in FIG. 5 the presence of the mask poses some difficulties for calculating the electric field image. In order to analyze images with masks, the calculation flow needs to be somewhat more sophisticated than described above. For non-pathological masks (e.g. the mask does not contain indentations) a logic procedure that seeks out a suitable reference pixel in a previous row when an adjacent pixel in the row is unavailable proves adequate. For pathological masks, a searching algorithm based on binary search methodologies can be utilized. The pixel array is treated as a digital algorithmic graph with each pixel being a vertex and connections existing between all nearest neighbor pixels that are not part of the mask. Either a breadth-first or depth-first search is then utilized to visit each nearest neighbor pixel and calculate its phase with the previously vertex pixel utilized as the phase reference. The theory of digital algorithmic graphs indicates that such a search will eventually visit all the connected pixels in the graph.

Figure 6:
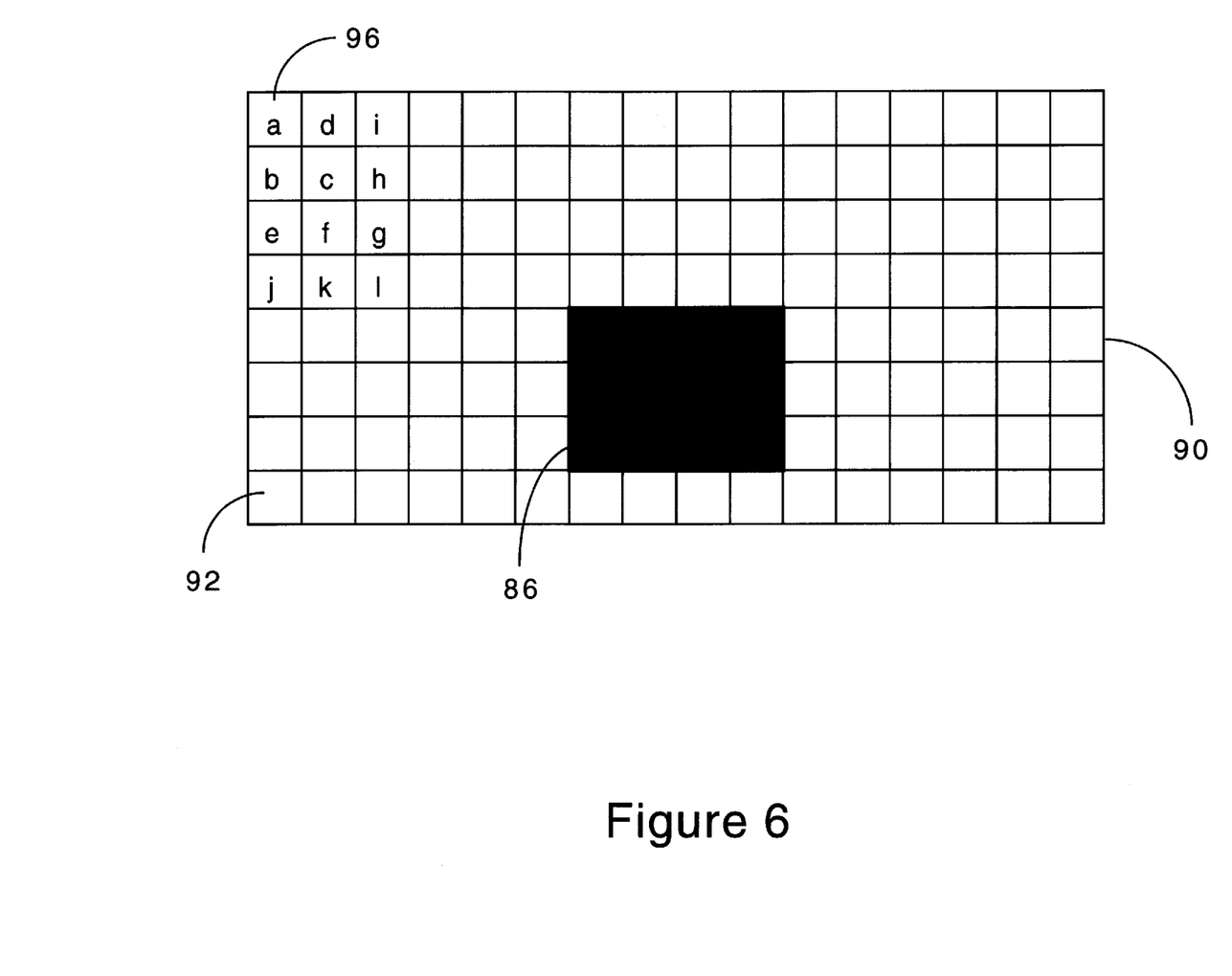
FIG. 6 is a schematic of the details of an alternate approach to the phase extraction process for each pixel in the image which utilizing breadth first processing techniques.

FIG. 6 shows the beginning of a breadth first search. Letters in each pixel indicate the order in which they are visited. Note that voids with the mask must be separately processed and calibrated. Pixel (a) is chosen is the initial reference pixel and first vertex of the search. In the breadth first search pixels (b), (c), and (d) are visited in order with pixel (a) used as the reference to determine their phases. Pixel (b) then becomes the new vertex. Its nearest neighbors (a), (c) and (d) have already been visited and are therefore ignored. Its nearest neighbors (e) and (f) have not been visited and their phase values are calculated using pixel (b) as the phase reference. In turn, pixel (c) is used for the phase reference for pixels (g), (h), and (i), pixel (e) is used for the phase reference for pixels (j) and (k), and so on. Masked pixels are ignored in this process. Several detailed digital methodologies for performing breadth first and depth first graph searches on digital methodologies for described in the field, which can be utilized in the current invention (see for example, Introduction to Algorithms, T. H. Cormen, C. E. Leiserson, and R. L. Rivest, MIT Press and McGraw-Hill, 465-97(1993)).

An additional extension of the electric field imaging system is the use of pulsed lasers to obtain time resolved images and sequences of images which can be strung together to generate a computer animation of movie. In this configuration, the laser pulse is synchronized with the electric field event. The laser pulse then produces an image of the electric field at a time when the pulse passes through the optically active media. For repetitive events, the time delay between the laser pulse and electric field event can be shifted in small increments with an image produced at each increment, thus producing a computer movie or animation.

While the preferred embodiment of the invention has been illustrated and described, it will be apparent that various changes can be made therein without departing from the spirit and scope of the invention.

The embodiments of the invention in which an exclusive property of privilege is claimed are defined as follows:

1. A method for quantitatively imaging the internal electric fields in an electro-optic media comprising
   a) passing an optical beam through polarizing means so that an initial polarization of the optical beam is produced;
   b) placing a target comprising electro-optic media and means for applying an electric field to said media in the path of the optical beam so that the optical beam passes from the polarizing means through the target;
   c) applying an electric field to the target, so that said electric field modifies the initial polarization of the optical beam passing through the target;
   d) passing the optical beam through analyzing means so that said polarization modifications are selectively passed or analyzed producing a spatial variation in the optical beam intensity which spatial variation is related to the electric field in the target;
   e) detecting the resultant spatial variation and producing a plurality of images of said spatial variation, said plurality of images comprising at least a background image, an X image, and a Y image, whereby said X image and Y image result from changing the state of the polarization and the analyzing means;
   f) pixelating, digitizing, and registering the background, X, and Y images;
   g) subtracting said background image intensity values from both the X image intensity values and Y image intensity values, followed by dividing the two resultant subtracted images, whereby an intermediate image array is produced with array values dependent on the tangent of a phase argument given by the electric field within the target times an electro-optic, media-dependent coefficient;
   h) processing the intermediate image array to invert the tangent dependency by referencing the phase argument of the tangent dependency of the electric field to an adjacent pixel and then inverting the tangent dependency of the current pixel, stepping from pixel-to-pixel as each new phase argument is calculated, whereby any phase redundancy in the phase argument is removed, said media-dependent coefficient is normalizes, and an electric field image of the target is produced; and
   i) displaying the electric field image.

2. The electric field imaging method of claim 1 further including marking means to mark areas of the image which are not to be processed and means to step from pixel-to-pixel such that all unmarked pixels are processed.

3. The electric field imaging method of claim 2 wherein the marking means comprises forming of a mask image in which the pixels not to be inverted are set to black or zero and all other pixels are set to white or full scale, combining said mask with the background image, the X image, and the Y image in such a fashion that the pixels in these images corresponding to the black pixels in the mask are set to zero and the remaining pixels are left unchanged, and utilizing the simultaneous appearance of zeros in the background, X and Y images as the mark indicator.

4. The electric field imaging method of claim 2 wherein the means to step from pixel-to-pixel comprises a depth-first or breadth-first search based on graphical computation methods defining each pixel as a vertex and a connection is made to each of all adjacent pixels which are not marked.

5. An electric field imaging system comprising
   a) an optical beam;
   b) polarizing means for setting the initial polarization of the optical beam;
   c) a target comprising an electro-optic material and electrical contacts, which is placed in the path of the optical beam such that the optical beam passes from said polarizing means through the target;
   d) means for applying an electric field to said target, whereby said electric field modifies the polarization of the optical beam passing through the target due to the electro-optic effect;
   e) analyzing means for selectively passing or analyzing the polarization of the optical beam after it has passed through said target;
   f) detection means for producing a plurality of images of the optical beam after passing through said analyzing means, whereby said plurality of images comprises at least abackground image, an X image, and a Y image, whereby said X image and Y image result from changing the state of the polarization and the analyzing means;
   g) processing means for registering the background, X and Y images, followed by performing computations in which the background image intensity values for each pixel are subtracted from the X image intensity values and Y image intensity values, and the two subtracted images are then divided producing an intermediate image array with values dependent on the tangent of the electric field of within the target;
   h) processing means for additionally inverting the tangent dependency of the intermediate image array by referencing the phase argument of the tangent dependency of the electric field to an adjacent pixel and then inverting the tangent dependency of the current pixel, stepping from pixel-to-pixel as each new phase argument is calculated, thereby removing the phase redundancy of the tangent inversion process;
   i) processing means for further normalizing the phase arguments with values related to the material properties of the target to produce the electric field image and removing an arbitrary constant resulting from the tangent inversion; and
   j) display means for displaying the electric field image.

6. The electric field imaging system of claim 5 further including means to mark areas of the image which are not to be processed and means to step from pixel-to-pixel such that all unmarked pixels are processed.

7. The electric field imaging system of claim 6 wherein the marking means comprises the formation of a digital mask image in which values of the pixels not to be inverted are set to zero and all other pixels are set with ones in all the bits, combining said mask with the background image, the X image, and the Y image with a Boolean AND so that the pixels in these images corresponding to the zero pixel values in the mask are set to zero and the remaining pixels are left unchanged, and utilizing the simultaneous appearance of zeros in the background, X and Y images as the mark indicator.

8. The electric field imaging system of claim 7 wherein the means to step from pixel-to-pixel comprises a depth-first or breadth-first search based on graphical computation methods defining each pixel as a vertex and connections to each of the adjacent pixels which is not marked.

9. The electric field imaging system of claim 5 wherein
   a) the detection means comprises an electronic camera; and
   b) the processing means comprises a frame grabber, which pixelates the image and digitizes the intensity of each image pixel and a general purpose computer for performing digital processing on image pixel values.

10. The electric field imaging system of claim 5 wherein the polarizing means comprises a linear polarizer, a half waveplate, and a quarter waveplate with the optical beam passing through said polarization means in the order of the linear polarizer, the half waveplate, and the quarter waveplate.

11. The electric field imaging system of claim 5 wherein the polarizing means comprises a polarizing beam splitter, a half waveplate, and a quarter waveplate with the optical beam passing through said polarization means in the order of the polarizing beam splitter, the half waveplate, and the quarter waveplate.

12. The electric field imaging system of claim 5 wherein the analyzing means comprises a quarter waveplate, a half waveplate, and a linear polarizer with the optical beam passing through said polarization means in the order of the quarter waveplate, the half waveplate, and the linear polarizer.

13. The electric field imaging system of claim 5 wherein the analyzing means comprises a quarter waveplate, a half waveplate, and a polarizing beam splitter with the optical beam passing through said polarization means in the order of the quarter waveplate, the half waveplate, and the polarizing beam splitter.

* * * * *